United States Patent
Martineau et al.

(10) Patent No.: US 11,332,782 B2
(45) Date of Patent: May 17, 2022

(54) METHOD FOR DETECTING NUCLEOTIDE POLYMORPHISMS

(71) Applicants: Rhett Martineau, Gilbert, AZ (US); Deirdre Meldrum, Phoenix, AZ (US)

(72) Inventors: Rhett Martineau, Gilbert, AZ (US); Deirdre Meldrum, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 379 days.

(21) Appl. No.: 16/323,397

(22) PCT Filed: Aug. 7, 2017

(86) PCT No.: PCT/US2017/045802
§ 371 (c)(1),
(2) Date: Feb. 5, 2019

(87) PCT Pub. No.: WO2018/027238
PCT Pub. Date: Feb. 8, 2018

(65) Prior Publication Data
US 2019/0177784 A1   Jun. 13, 2019

Related U.S. Application Data

(60) Provisional application No. 62/371,617, filed on Aug. 5, 2016.

(51) Int. Cl.
*C12Q 1/6858* (2018.01)
*C12Q 1/6883* (2018.01)
*C12N 9/12* (2006.01)
*C12N 15/09* (2006.01)

(52) U.S. Cl.
CPC .......... *C12Q 1/6858* (2013.01); *C12N 9/12* (2013.01); *C12N 15/09* (2013.01); *C12Q 1/6883* (2013.01); *C12Q 2600/156* (2013.01)

(58) Field of Classification Search
CPC ............ C12Q 1/6858; C12Q 1/6883; C12Q 2600/156
See application file for complete search history.

(56) References Cited

U.S. PATENT DOCUMENTS

| | | | |
|---|---|---|---|
| 9,410,970 B2 | 8/2016 | Tian et al. | |
| 9,597,026 B2 | 3/2017 | Meldrum et al. | |
| 10,022,718 B2 | 7/2018 | Martineau et al. | |
| 10,162,162 B2 | 12/2018 | Wang et al. | |
| 10,221,443 B2 | 3/2019 | Meldrum et al. | |
| 10,260,090 B2 | 4/2019 | Martineau et al. | |
| 10,378,019 B2 | 8/2019 | Wang et al. | |
| 10,391,485 B2 | 8/2019 | Meldrum et al. | |
| 10,471,426 B2 | 11/2019 | Martineau et al. | |
| 2012/0171676 A1* | 7/2012 | Adlerstein | C12Q 1/6858 435/6.11 |
| 2012/0231533 A1 | 9/2012 | Holl et al. | |
| 2012/0276538 A1 | 11/2012 | Nadeau | |
| 2013/0323793 A1 | 12/2013 | Tanner et al. | |
| 2015/0253333 A1 | 9/2015 | Tian et al. | |
| 2016/0076083 A1 | 5/2016 | Ellington et al. | |
| 2016/0202247 A1 | 7/2016 | Tian et al. | |
| 2016/0215254 A1 | 7/2016 | Meldrum et al. | |
| 2018/0264468 A1 | 9/2018 | Anderson et al. | |
| 2018/0334700 A1 | 11/2018 | Messner et al. | |

(Continued)

FOREIGN PATENT DOCUMENTS

| | | |
|---|---|---|
| WO | 2010022391 A2 | 2/2010 |
| WO | 2010022391 A9 | 2/2010 |

(Continued)

OTHER PUBLICATIONS

Cukjati, M. et al., "Prevalence of H63D, S65C and C282Y hereditary hemochromatosis gene mutations in Slovenian population by an improved high-throughput genotyping assay", BMC Medical Genetics, Nov. 2007, vol. 8, No. 69, 9 pages <DOI:10.1186/1471-2350-8-69>.

Baniecki, M. et al., "Development of a Single Nucleotide Polymorphism Barcode to Genotype Plasmodium vivax Infections", Neglected Tropical Diseases, Mar. 2015, vol. 9, No. 3, article e0003539, 18 pages <DOI:10.1371/journal.pntd.0003539>.

Begovich, A. et al., "A Missense Single-Nucleotide Polymorphism in a Gene Encoding a Protein Tyrosine Phosphatase (PTPN22) Is Associated with Rheumatoid Arthritis", AJHG, Aug. 2004 (available online Jan. 2008), vol. 75, No. 2, pp. 330-337 <DOI:10.1086/422827>.

(Continued)

*Primary Examiner* — Samuel C Woolwine
*Assistant Examiner* — Carolyn L Greene
(74) *Attorney, Agent, or Firm* — Lee & Lin IP PLLC; Jeong Lee-Nago; Rita H. Lin

(57) ABSTRACT

Methods for detecting single nucleotide polymorphisms in nucleotide sequences using LAMP reactions are provided herein. Generally, two sets of LAMP primers, a wild-type primer that matches expected DNA sequences and an SNP primer that matches the expected SNP DNA are provided. One method includes providing the wild-type primer and the SNP primer in separate wells of a multi-well microfluidic array device, adding the sample nucleotide sequence into the wells seeded with the primers, and initiating LAMP reactions within the wells. The method includes observing the reaction differential between the primers and determining the status of the DNA with regard to that particular SNP. A second method includes providing the primers with tags in a mixture, adding the sample nucleotide sequence to the mixture, and initiating LAMP reactions. The method includes providing a different visual indication when the wild-type primer reacts with the sample nucleotide sequence versus when the SNP primer reacts with the sample nucleotide sequence, and determining the status of the DNA with regard to that particular SNP.

12 Claims, 9 Drawing Sheets

Specification includes a Sequence Listing.

(56) References Cited

U.S. PATENT DOCUMENTS

| | | | |
|---|---|---|---|
| 2019/0126275 A1 | 5/2019 | Kelbauskas et al. | |
| 2019/0346361 A1 | 11/2019 | Meldrum et al. | |

FOREIGN PATENT DOCUMENTS

| | | |
|---|---|---|
| WO | 2010042478 A2 | 4/2010 |
| WO | 2010062654 A2 | 6/2010 |
| WO | 2015048009 A1 | 4/2015 |
| WO | 2017049122 A1 | 3/2017 |
| WO | 2017062807 A1 | 4/2017 |
| WO | 2017083817 A1 | 5/2017 |
| WO | 2017087473 A1 | 5/2017 |
| WO | 2017151978 A1 | 9/2017 |
| WO | 2017184998 A1 | 10/2017 |
| WO | 2018027236 A1 | 2/2018 |
| WO | 2018027238 A1 | 2/2018 |
| WO | 2018157064 A1 | 8/2018 |
| WO | 2018160998 A1 | 9/2018 |
| WO | 2018213269 A1 | 11/2018 |
| WO | 2019046452 A1 | 3/2019 |

OTHER PUBLICATIONS

Duan, Y. et al., "Development and application of loop-mediated isothermal amplification for detecting the highly benzimidazole-resistant isolates in Sclerotinia sclerotiorum", Scientific Reports, Nov. 2015, vol. 5, No. 17278, 11 pages <DOI:10.1038/srep17278>.

Duan, Y. et al., "Development and application of loop-mediated isothermal amplification for detection of the F167Y mutation of carbendazim-resistant isolates in Fusarium graminearum", Scientific Reports, Nov. 2014, vol. 4, No. 7094, 8 pages <DOI:10.1038/srep07094>.

Hoshi, K. et al., "Rapid Detection of Epidermal Growth Factor Receptor Mutations in Lung Cancer by the SMart-Amplification Process", Clinical Cancer Research, Sep. 2007, vol. 13, No. 17, pp. 4974-4983 <DOI:10.1158/1078-0432.CCR-07-0509>.

Iwasaki, M. et al., "Validation of the Loop-Mediated Isothermal Amplification Method for Single Nucleotide Polymorphism Genotyping with Whole Blood", Genome Letters, Sep. 2003, vol. 2, No. 3, pp. 119-126 <DOI:10.1166/gl.2003.028>.

Kubota, R. et al., "Real-Time Duplex Applications of Loop-Mediated AMPlification (LAMP) by Assimilating Probes", International Journal of Molecular Sciences, Mar. 2015, vol. 16, No. 3, pp. 4786-4799 <DOI:10.3390/ijms16034786>.

Lezhava, A. et al., "Exciton Primer-mediated SNP detection in SmartAmp2 reactions", Human Mutation, Feb. 2010 (available online Jan. 2010), vol. 31, No. 2, pp. 208-217 <DOI:10.1002/humu.21177>.

MacLeod, J. et al., "Fast, sensitive point of care electrochemical molecular system for point mutation and select agent detection", Lab on a Chip, Jun. 2016, vol. 16, No. 13, pp. 2513-2520 <DOI:10.1039/c5lc01532d>.

Marasso, S. et al., "A polymer Lab-on-a-Chip for genetic analysis using the arrayed primer extension on microarray chips", Biomedical Microdevices, Oct. 2014 (available online May 2014), vol. 16, No. 5, pp. 661-670 <DOI:10.1007/s10544-014-9869-x>.

Mitani, Y. et al., "Rapid SNP diagnostics using asymmetric isothermal amplification and a new mismatch-suppression technology", Nature Methods, Mar. 2007 (available online Feb. 2007), vol. 4, No. 3, pp. 257-262 <DOI:10.1038/nmeth1007>.

Nübel, U. et al., "Single-Nucleotide Polymorphism Genotyping Identifies a Locally Endemic Clone of Methicillin-Resistant *Staphylococcus aureus*", PLoS One, Mar. 2012, vol. 7, No. 3, article e32698, 5 pages <DOI:10.1371/journal.pone.0032698>.

Pardee, K. et al., "Rapid, Low-Cost Detection of Zika Virus Using Programmable Biomolecular Components", Cell, May 2016, vol. 165, No. 5, pp. 1255-1266 <DOI:10.1016/j.cell.2016.04.059>.

Patent Cooperation Treaty, International Searching Authority, International Preliminaary Report on Patentability and Written Opinion for PCT/US2017/045802, 9 pages, report dated Feb. 5, 2019, opinion dated Oct. 24, 2017.

Patent Cooperation Treaty, International Searching Authority, International Search Report for PCT/US2017/045802, 3 pages, dated Oct. 24, 2017.

Roche Diagnostics., "FDA Grants First Liquid Biopsy Approval to the Roche cobas® EGFR Mutation Test v2" [online], Roche Diagnostics, Jun. 2016 [retrieved on Dec. 2, 2019], retrieved from the internet: <URL:https://diagnostics.roche.com/us/en/news-listing/2016/fda-grants-first-liquid-biopsy-approval-to-the-roche-cobas-egfr-mutation-test-v21.html>.

Stephens, A. et al., "Methicillin-resistant *Staphylococcus aureus* genotyping using a small set of polymorphisms", Journal of Medical Microbiology, Jan. 2006, vol. 55, Pt. 1, pp. 43-51 <DOI:10.1099/jmm.0.46157-0>.

Tani, H. et al., "Technique for Quantitative Detection of Specific DNA Sequences Using Alternately Binding Quenching Probe Competitive Assay Combined with Loop-Mediated Isothermal Amplification", Analytical Chemistry, Aug. 2007 (available online Jun. 2007), vol. 79, No. 15, pp. 5608-5613 <DOI:10.1021/ac070041e>.

Tanner, N. et al., "Simultaneous multiple target detection in real-time loop-mediated isothermal amplification", Biotechniques, Aug. 2012 (available online Apr. 2018), vol. 53, No. 2, pp. 81-89 <DOI:10.2144/0000113902>.

The UK Haemochromatosis Consortium., "A simple genetic test identifies 90% of UK patients with haemochromatosis", Gut, 1997, vol. 41, No. 6, pp. 841-844.

Zhang, C. et al., "Establishment and application of a real-time loop-mediated isothermal amplification system for the detection of CYP2C19 polymorphisms", Scientific Reports, Jun. 2016, vol. 6, No. 26533, 7 pages <DOI:10.1038/srep26533>.

U.S. Appl. No. 15/774,558.
U.S. Appl. No. 15/774,563.
U.S. Appl. No. 16/203,365.
U.S. Appl. No. 16/323,393.
U.S. Appl. No. 16/479,729.
U.S. Appl. No. 16/487,535.
U.S. Appl. No. 16/611,799.

Notification of Transmittal of International Search Report and the Written Opinion of the International Searching Authority, or the Declaration PCT/US2017/045802.

Zhang et al. "Establishment and Application of a Real-Time Loop-Mediated Isothermal Amplification System for the Detection of CYP2C19 Polymorphisms," Scientific Reports.

Tanner et al. "Simultaneous Multiple Target Detection in Real-Time Loop-Mediated Isothermal Amplification," BioTechniques, Aug. 1, 2012.

Kubota, et al. "Real Time Duplex Appplications of Loop-Mediated Amplification (LAMP) by Assimilating Probes," Int J Mol Sci Mar. 3, 2015.

\* cited by examiner

FIG. 2

Primer (5' → 3')

| | |
|---|---|
| FIP-wt | CACGTATATCTCTGCTCTTGGGATGGGACCTACCAGGGCT |
| FIP-SNP | *T*ACGTATATCTCTGCTCTTGGGATGGGACCTACCAGGGCT |
| | F1c  *  F2 |

Wild-type allele

5'-CGAACCTAAAGACGTATTGCCCAATGGGGATGGGACCTACCAGGGCTGGATAACCTTGGCTGTACCCCCTGGGAAGAGCAGAGATATACG|TGC|AGG
                                           F2                                               |||||||||||||||||||||||
                                                                                          TTCTCGTCTCTATATGCAC-5'
                                                                                          F1
                                                                                          FIP-wt F1c

SNP allele

5'-CGAACCTAAAGACGTATTGCCCAATGGGGATGGGACCTACCAGGGCTGGATAACCTTGGCTGTACCCCCTGGGAAGAGCAGAGATATACG|TAC|AGG
                                           F2                                               |||||||||||||||||||||||
                                                                                          TTCTCGTCTCTATATGCAT-5'
                                                                                          FIP-SNP F1c

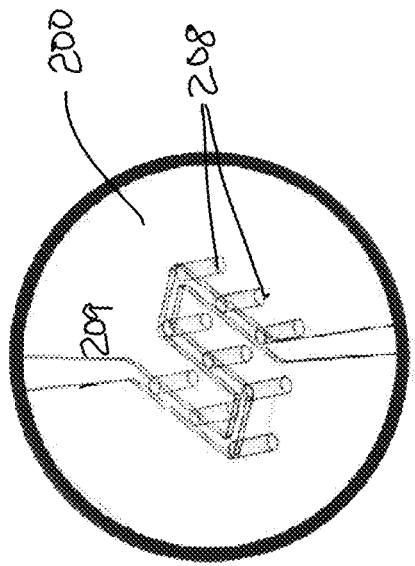
FIG. 3B
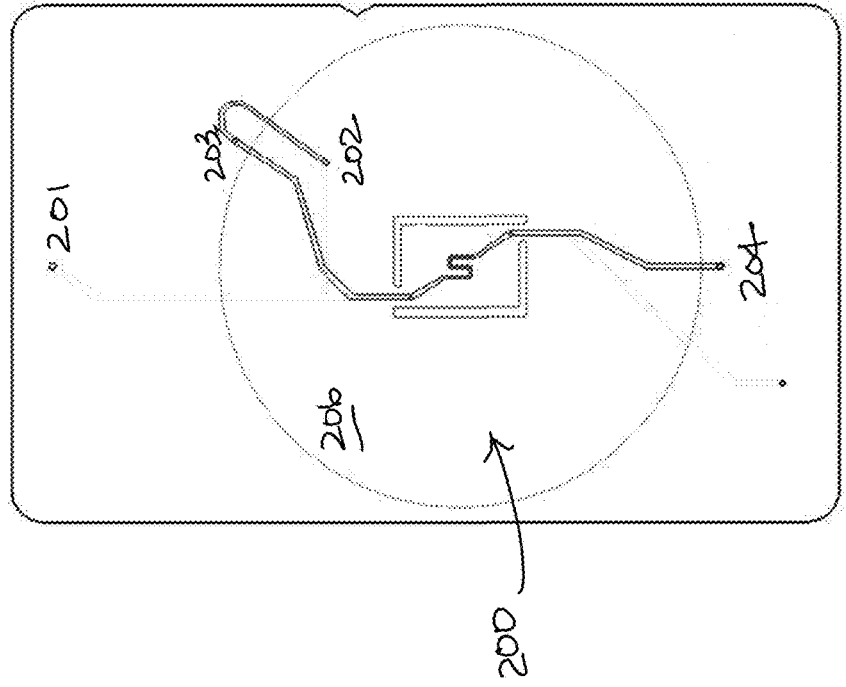
FIG. 3C
FIG. 3A

FIG. 5

Table 1. Array-based SNP differentiation

| Sample constituency | Wild-type primer response | Mismatch primer response |
|---|---|---|
| Homozygous, healthy | + | - |
| Heterozygous, healthy | + | + |
| Homozygous, disease | - | + |

METHOD FOR DETECTING NUCLEOTIDE POLYMORPHISMS

CROSS REFERENCE TO RELATED APPLICATION

The application claims the benefit of PCT/US17/45802, titled "METHOD FOR DETECTING NUCLEOTIDE POLYMORPHISMS," filed Aug. 7, 2017, which claims priority to U.S. provisional application No. 62/371,617, titled "DEVICE AND METHOD FOR SINGLE NUCLEOTIDE POLYMORPHISM DETECTION," filed Aug. 5, 2016. Both are incorporated by reference herein in their entirety.

The application is the national stage of PCT/US17/45802 filed on Aug. 7, 2017, which claims the benefit of United States Provisional Application No. 62/371,617, filed on Aug. 5, 2016, which are incorporated by reference herein in their entirety.

FIELD OF INVENTION

The invention is related to methods for detecting single nucleotide polymorphisms in nucleotide sequences.

BACKGROUND OF THE INVENTION

The invention relates generally to detecting nucleotide polymorphisms (SNPs), also referred to as "mutations," in nucleotide sequences, and preferably methods and systems for low-cost SNP genotyping of Deoxyribonucleic acid (DNA) samples.

Single nucleotide defects in a gene or regulatory element may have significant impact on the activity of critical proteins. Results may include altered susceptibility to pharmaceutical compounds or even the manifestation of disease, for example hemochromatosis, wherein a single nucleotide mismatch causes a mistranslation of a single amino acid, resulting in impaired protein function. When an individual is homozygous for the defect, iron transport is impaired and the symptoms of the disease manifest.

The standard methods for SNP typing are generally based on sequencing. Modern sequencers are relatively cost effective compared to earlier sequencers, but even modern sequencers still generally require a laboratory setting and skilled technicians, which may make the cost of analysis significant. Efforts toward establishing methods for SNP detection in low-cost formats are active, with Abbott Laboratories, as an example, recently publishing a chip-based, hand-held electrochemical PCR (Polymerase chain reaction) method targeting the most prevalent SNP found in human hemochromatosis.

Common methods to detect single nucleotide polymorphisms that do not require sequencing are in general expensive and require skilled technicians and specialized equipment. Assays based on PCR are generally the most popular. PCR-based methods for SNP detection have been in existence for several decades, but the stringent analytical requirements of PCR generally make the assay more complex, and thus more expensive, than newer methods. In particular, isothermal nucleic acid amplification techniques offer important advantages in reduced complexity and cost. Thus, although the Abbott approach offers significant reductions in cost and user expertise, approaches based on isothermal techniques have the potential to be just as simple to use but more cost effective.

The reliability of the technique in general may depend upon the specifics of LAMP target and primers. Lack of 100% reliability has given rise to numerous attempts to improve the situation. For example, a mismatch-sensing protein MutS was added to the reaction, which was reportedly highly effective at blocking primer extension through mismatches. However, although LAMP-based SNP tests appear to have been commercialized by DNAFORM (Japan), these do not appear to be available for use in diagnosis in humans. Thus, some of the most significant uses of the technology are precluded. The reason for lack of clearance for human use is unclear. On the other hand, Roche Diagnostics provides a PCR-based approach for a recently FDA (Food and Drug Administration)-cleared test kit 'cobas EGFR mutation test v2' (See molecular.roche.com). PCR-based tests, however, do not enjoy many of the numerous advantages offered by LAMP-based assays.

The reliability of the technique in general may depend upon the specifics of LAMP target and primers. Lack of 100% reliability has given rise to numerous attempts to improve the situation. For example, a mismatch-sensing protein MutS was added to the reaction, which was reportedly highly effective at blocking primer extension through mismatches. However, although LAMP-based SNP tests appear to have been commercialized by DNAFORM (Japan), these do not appear to be available for use in diagnosis in humans. Thus, some of the most significant uses of the technology are precluded. The reason for lack of clearance for human use is unclear. On the other hand, Roche Diagnostics provides a PCR-based approach for a recently FDA (Food and Drug Administration)-cleared test kit 'cobas EGFR mutation test v2' (See https://molecular.roche.com/news/fda-grants-first-liquid-biopsy-approval-to-the-rochecobas-egfr-mutation-test-v2/, cleared June of 2016). PCR-based tests, however, do not enjoy many of the numerous advantages offered by LAMP-based assays.

In another case, rather than a single mismatch between an SNP and a 5' terminal base on the FIP, two single mismatched bases on both FIP and BIP primers were provided by removing the 'Stem region' (between F1 and B1), such that both primers FIP and BIP loop back on the same mismatched primer. This approach reportedly differentiated SNPs with a rate of 100%. That is, primers that possessed no mismatches were always effective at both correctly amplifying matched targets and not amplifying mismatched targets at all. However, the data presented in the report do not make a strong case for this assertion, as only small, hand-picked datasets were presented. Furthermore, since the single-primer mismatch approach yields a finite level of false positives, it is reasonable to assume that the double-primer mismatch approach will likewise exhibit a finite level of false positives, albeit at a lower rate. Even if the double-primer mismatch approach is as good as initial research claims, there is very little tolerance toward primer design as both FIP and BIP primers are locked in their positions, greatly limiting the assay designer's ability to navigate around assay design difficulties associated with the desired target sequence.

Accordingly, it is desirable to provide a method and system for detecting SNPs that overcomes drawbacks and inadequacies of known methods and systems.

SUMMARY OF THE INVENTIONS

Generally speaking, in accordance with an embodiment of the invention, a method of detecting an SNP is based on an isothermal nucleic acids amplification technique known as loop-mediated isothermal amplification (LAMP), coupled with novel priming, microfluidic partitioning, specialized primer design and/or statistical approaches to enable low-cost and improved accuracy in SNP typing.

An embodiment of the invention provides for performing a number of LAMP reactions as a collective assay in a multi-well microfluidic array seeded with a set of primers differing in their FIP or BIP primer in the 5' region, such that the first set matches the wild-type allele and the second set matches the SNP allele. The sample DNA is added thereafter into the wells and the rates of reaction of the primers are compared to determine whether or not the DNA sample is homozygous for the wild-type allele, the SNP allele, or heterozygous for the SNP of interest.

Another embodiment of the invention provides adding primers targeting reference sequences in reference wells to target a conserved region in the targeted genome to establish a reference reaction.

In another embodiment, reference primers and reference DNA are added to establish a positive control.

Yet other embodiments of the invention are directed to competition assays comprising adding wild-type primers and SNP primers which compete for the same spot on the allele with a sample DNA. Depending on which primer reacts more in the sample, the status of the DNA with regard to that particular SNP may be determined.

Still other objects and advantages of the invention will in part be obvious and will in part be apparent from the specification. Other features and advantages of this invention will become apparent in the following detailed description of exemplary embodiments of this invention with reference to the accompanying drawings.

BRIEF DESCRIPTION OF THE DRAWINGS

For a fuller understanding of the invention, reference is made to the following description taken in connection with the accompanying drawing, in which:

FIG. 2 illustrates a sample wild-type primer, SNP primer, wild-type allele and SNP allele;

FIG. 3A is a schematic view of a microfluidic array device utilized in accordance with an embodiment of the invention;

FIG. 3B is a detailed perspective view of the microfluidic array device of FIG. 3A;

FIG. 3C is an illustration of the wells of the microfluidic array device of FIG. 3A seeded with their respective primer;

FIG. 5 is a table for array-based SNP differentiation in accordance with an embodiment of the invention;

DETAILED DESCRIPTION OF THE PREFERRED EMBODIMENTS

The invention generally is directed to SNP detection utilizing nucleic acid amplification technology, more particularly to isothermal amplification techniques such as loop-mediated isothermal amplification (LAMP).

In the interest of reducing cost per assay, SNP typing based on LAMP and visual detection may be preferred. A simple visual readout, preferably on a portable, handheld device such as a cell phone, may also facilitate analysis through image processing. Thus, due to the prevalence of low-cost imaging equipment with integral processing power (i.e., handheld devices such as cell phones), SNP typing may be done objectively without requiring the use of specialized laboratory equipment or dedicated handheld readers. Thus, cost is preferably kept to a minimum while maintaining a high quality and repeatability of the assay. In conclusion, inventors discovered that there is value in a LAMP-based, visual indicator device that is capable of distinguishing SNPs.

Figure 1:
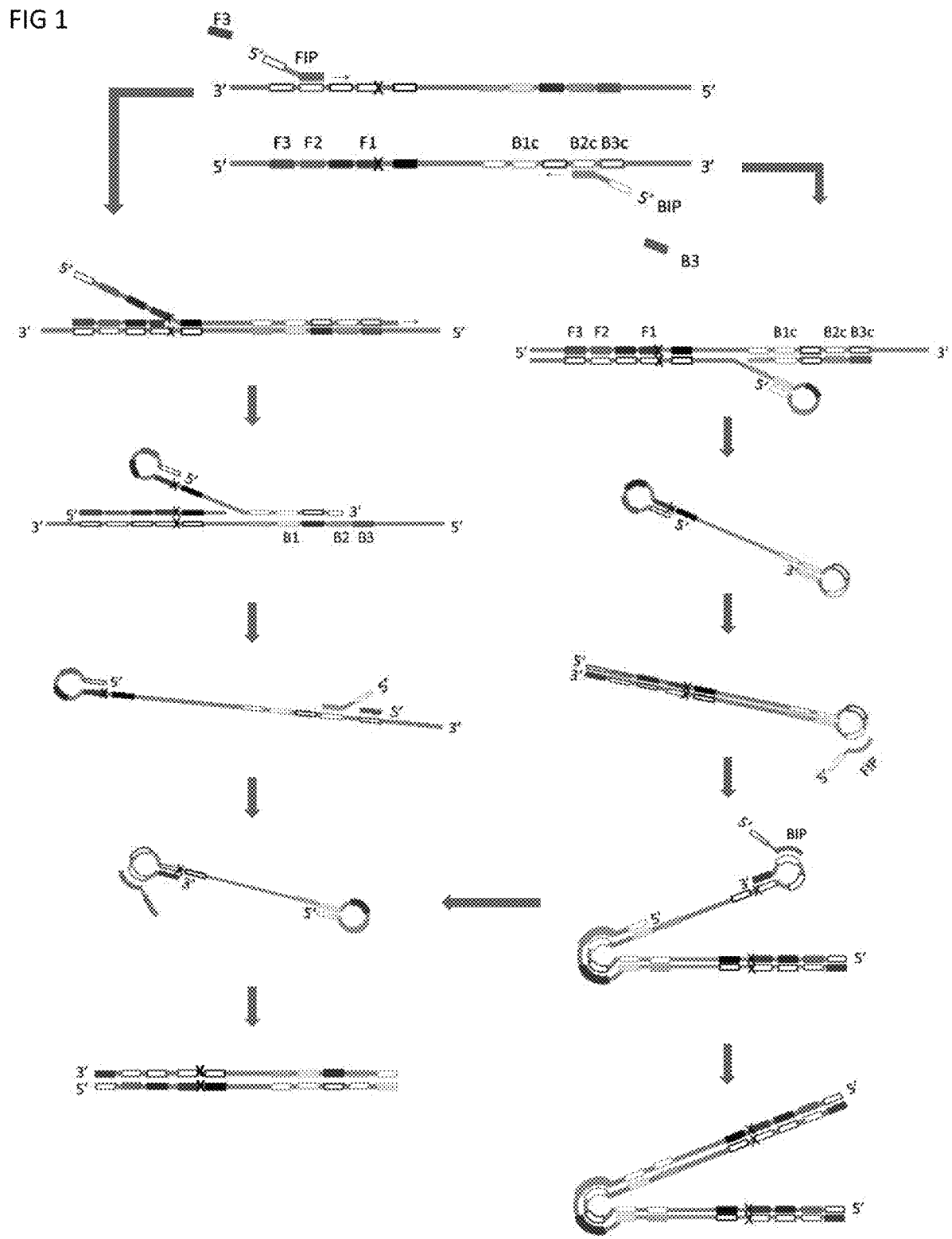
FIG. 1 is an illustration of a series of reactions in accordance with an embodiment of the invention.

The foundation of an embodiment of the invention is the loop mediated isothermal amplification (LAMP) reaction. There are two approaches to SNP detection based on conventional LAMP. The general idea is to develop two sets of LAMP primers, one that matches expected DNA sequences perfectly and one that matches the expected SNP DNA perfectly. The match/mismatch identification component of the primer sets is placed in two regions on the LAMP primers. A preferred method is to create a single base mismatch at the 5' extreme on the forward inner primer (FIP) primer (or, equivalently on the BIP primer), such that loop-back and extension is inhibited, as is shown in FIG. 1. As shown, "X" represents a mismatched base, for example, an SNP. A wild-type FIP primer that matches the expected "wild" DNA sequence would mismatch at the X in the gene target and at the 5' region of the primer. The reactions will likely be slower compared to those of a perfectly matched primer.

FIG. 1 illustrates LAMP reactions that are stifled by the presence of SNP's. In particular, 3' extensions through SNPs are inhibited. The result is double-stranded amplicons that are cycled inefficiently, hindering extensive LAMP reaction.

Another approach entails placing the single base mismatch at the 3' end of the FIP primers. Whereas acceptable, it is less preferred because false read-throughs may be more common and thus the ability to discern between single base changes may be more significantly compromised. Even when the base mismatch is sensed via the 5' end of the FIP primer, a significant number of 'false positives' may occur, and thus comparisons between multiple replicates may generally be required.

Two methods of establishing low-cost, easy to use, accurate and reliable diagnostics for SNPs are described herein: 1. Microfluidic, arrayed SNP primer sets; and 2. SNP Primer competition assays. Whereas SNP detection methods in DNA are addressed herein, SNP detection in RNA (for example, RNA viruses or expressed genes) is likewise possible by incorporating reverse transcriptases into the reactions, as is known to those skilled in the art.

Microfluidic, Arrayed SNP Primer Sets

An embodiment of the first method described herein is based on assessing the SNP content of a sample by performing a number of LAMP reactions as a collective assay. A multi-well microfluidic array device is preferably provided and seeded with at least two sets of target-specific LAMP primers. It may be preferred to include more sets of primers to increase response confidence, for example, two reference primer sets. The first primer set is placed in a first set of wells, and the second primer set in a second set of wells. The exemplary sets of primers differ from each other in either their 5' or 3' sequence or both, preferably, the 5' end of the primers, to confer SNP discernment. The two primer sets preferably differ from each other in their FIP or BIP primer (backward inner primer) in the 5' region, preferably only in the 5' region, such that the first set of primers (wild-type primers) matches the wild-type allele perfectly and the second set of primers (SNP primers) matches the SNP allele perfectly. The mismatch need not be at the 5' extreme, but preferably at the most destabilizing position given the reaction constraints. For example, the mismatch may occur at the second to the last base from the 5' end, determined by thermodynamic estimation or experiment, or on the 3' end by like considerations. Preferably, reference primers targeting reference sequences are added to reference wells to target a conserved region in the targeted genome, establishing a reference reaction. In another embodiment, reference primers and reference DNA are added to establish a positive control.

Reference is made to FIG. 2, wherein exemplary primers and alleles in accordance with an embodiment of the invention are illustrated. More particularly, FIG. 2 shows the details of establishing LAMP primers to exhibit reactions with differential reaction rates. The illustrated example shows differential reactions established by a single mismatch in the 5' region of FIP primers. Two types of primers are shown: a wild-type primer 302 designed to anneal perfectly to wild-type alleles 304, and an SNP primer 312 designed to anneal perfectly to SNP alleles 314. Conversely, wild-type primers 302 amplify SNP alleles 314 less efficiently, and likewise the SNP primers 312 amplify wild-type alleles 304 less efficiently. Other primers, for example, BIP, LF/LB, F3/B3 and others known in the art, may be included in the wild-type primer set and SNP primer set preferably in equal concentrations.

The primers 302, 312 are shown, in the top portion of FIG. 2, to differ by a single base at the 5' end (marked with an asterisk). The F2 portion of each, which binds to the target DNA complementary to the F2 region on both the wild-type allele 304 and SNP allele 314 is also illustrated. According to the amplification process of LAMP as understood in the art, the FIP primers 302, 312 bind to the strand opposite the F2 region of the alleles 304, 314 and extend from 5' to 3'. The 5' end of each primer then flips over and anneals to its own extension product, as illustrated for both alleles. The sequence for both the wild-type primer 302 (FIP-wt) and SNP primer 312 (FIP-SNP) are shown as they would anneal to their extension products. In this case, each primer 302, 312 is shown annealed to its respective target sequence. Both primers 302, 312 as shown in relation to their targets are expected to amplify optimally. If the primers are switched, however, then a base mismatch at the 5' extreme of the primer is expected, as well as a stifled amplification as discussed above. The two alleles 304, 314 are shown to differ by a single base in the boxed region in F1.

Whereas the examples of the wild-type and SNP primers are FIP primers, it is to be understood that BIP primers may be used instead to establish differential amplification efficiency without deviating from the scope of the invention.

Many types of microfluidic device are known in the art and are in general suitable for conducting the assays. In the embodiment illustrated in FIGS. 3A-C, a 9-well microfluidic device 200 having 9 wells 208 is utilized, wherein 4 replicates each of a set of wild-type primers 222 and a set of SNP primers 224 are provided, as well as one set of positive control primers 226. In FIG. 3A, a top-view of a 9-well device 200 is shown. FIG. 3B shows a detailed view of the wells 208 and a serpentine loading channel 209 over the wells 208. The illustrated device 200 is comprised of layers of thermally bonded polymer. The replicate numbers may be varied as desired, for example, depending on the quality of the primers for a given application. Preferably the replicate numbers range from 3-50 for each target.

In the embodiment illustrated, a sample containing DNA of interest is loaded into the wells according to one or more of the various methods known in the microfluidics art, and the set of reactions are conducted in parallel. In one example, vacuum applied to a manifold beneath the well array causes vacuum through the well floor, such as a hydrophobic membrane 206, to cause the DNA sample to load sequentially in the wells through the serpentine loading channel 209 above the wells.

Preferably, the wells 208 are then filled with the DNA solution, and an immiscible fluid compatible with buffered LAMP reactions is loaded over the wells to isolate the reactions, preferably via techniques known in the art. By loading each reaction well with lyophilized LAMP reagents and indicator systems, such as those known in the art (turbidometric, colorimetric, fluorescent, electrochemical, etc.), the reaction characteristic of each well after a set time following reaction initiation may be used to infer whether the two primer sets are responding differentially to the DNA sample.

According to an exemplary method, fluid containing a sample of interest and pre-mixed with LAMP reagents (except primers) is introduced at site 204, and vacuum is applied at site 201. A hydrophobic membrane 206 forms the base of the wells 208 such that vacuum applied at 201 causes fluid at 204 to be drawn through the serpentine channel 209, over the reaction wells 208 (previously loaded with primer and/or reference or control DNA), down into the reaction wells 208 until the fluid contacts the hydrophobic membrane 206, and then past site 203 until it stops at site 202, which contains a through-hole to the hydrophobic membrane 206.

Continuing to provide vacuum at this point preferably does not cause any further fluid motion, but may be preferable to degas the sample solution. Finally, water is passed from 205 to 201, and oil is passed through the serpentine channel 209 to seal and isolate the individual wells 208. FIG. 3C details the primer loading into wells 208. A plurality of first wells 212 contains primers targeting wild-type alleles; a plurality of second wells 214 contains primers targeting SNP alleles; and one reference well 216 contains positive control primers and DNA to establish a positive control on-chip. Once the sample is loaded into wells 208, and the wells 208 are hydrated from beneath the hydrophobic membrane 206 and isolated above with oil, the area under the wells 208 is heated to reaction temperature and the reactions are monitored according to standard procedures (colorimetry, fluorescence, etc.) as routinely applied by those skilled in the art.

The reaction may be initiated by elevating the temperature to 60-65 C, depending on the specific reaction's optimum preferably determined through experimentation. Various techniques known to those skilled in the art may be used for this purpose. In a preferred embodiment, a battery pack on the disposable reactor passes current through a resistance element manufactured in close proximity to the wells to create the required reaction temperature. Other approaches known in the art include placing the chip into an oven, into a dedicated heater/reader, by activating exothermic chemicals which melt temperature-setting waxes, and other methods.

In the embodiment illustrated in FIG. 3C, control primers 226 targeting reference sequences are added to the reference wells to target a conserved region in the targeted genome, establishing a reference reaction. In another embodiment, reference primers and reference DNA may be added to establish a positive control. Alternatively, positive controls may be based on seeding known concentrations of known alleles, for example, HFE_wt (HFE wild-type allele), HFE_SNP (HFE SNP allele), or Ref1 (Reference allele) with appropriate primers.

Figure 4A:
FIG. 4A is an illustration of a wild-type allele and an SNP-allele.
Figure 4B:
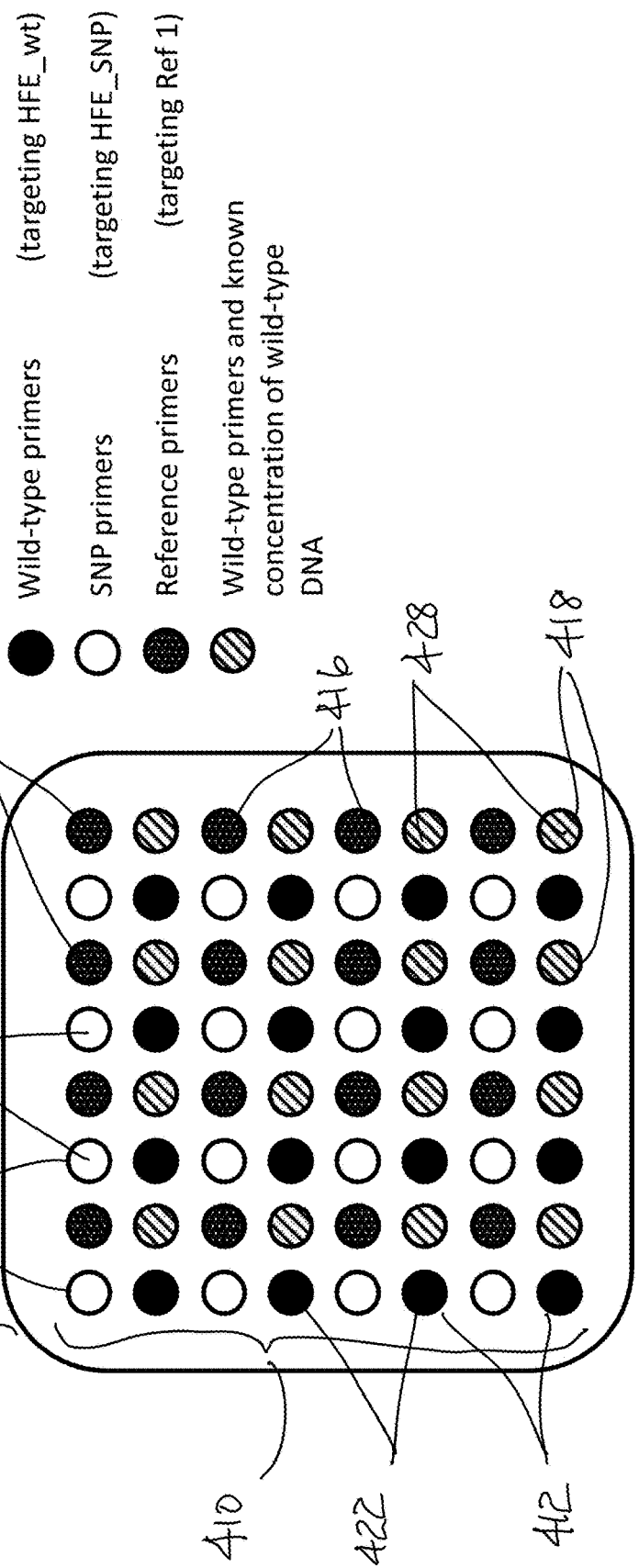
FIG. 4B is an illustration of the wells of the microfluidic array device seeded with their respective primer for the alleles of FIG. 4A.

Reference is made to FIGS. 4A and 4B, which illustrate an example of how a multi-well device 400 may be configured with multiple reaction replicates, reference reactions, and positive (or negative) controls. Two alleles of the HFE gene involved in the disease state in humans known as hemochromatosis are illustrated in FIG. 4A: HFE-wt allele 402, and HFE-SNP allele 404. If an SNP occurs in both alleles, the disease state exists in the individual. If only one copy of the gene contains the SNP, the disease does not manifest in the individual. However, the individual is a carrier and may propagate a mutation to offspring who then may have double mutant SNP alleles and exhibit effects of the disease. If two wild-type genes exist then the individual is healthy and will guarantee that offspring do not suffer hemochromatosis associated with this particular locus. A known reference region (Ref 1) is selected in an area of DNA that is the same on both copies 402, 404 in the individual and in a given population.

Referring to FIG. 4B, wells 410 are loaded with wild-type primers 422 in wild-type wells 412, SNP primers 424 in SNP wells 414, reference primers 426 targeting Ref 1 in reference wells 416, and wild-type primers with known concentrations of DNA 428 in control wells 418 to establish positive controls. The number of replicates preferably varies with the LAMP amplification characteristics, and more wells may be preferred for some systems than others. Reactions in reference wells may be used to establish that the target DNA was properly delivered to the device 400. Positive control reactions may be used to establish that the LAMP amplification reagents are functioning properly. If the reactions occur properly in the reference wells 416 and control wells 418, then the average reaction rates in the SNP wells 414 and wild-type wells 412 may be computed and compared. Alternately, the number of wells exhibiting reactions in a given time frame may be compared to establish differential activity of the two primer sets.

Differences/similarities in reaction rates may be compared to infer the constituency of the sample, as shown in Table 1 in FIG. 5. An embodiment of the invention provides for three different results, each indicating a different status of the individual from whom the sample DNA was acquired for testing. For example, each primer's rate of reaction compared to the other primer's rate of reaction may indicate the status of the DNA sample. The rate of reaction preferably refers to either the speed of reaction or the number of wells reacting within a certain period of time.

Namely, if the rate of reaction of the wild-type primer 422 and the SNP primer 424 are the same (indicated in Table 1 as + for both wild-type primer and SNP primer columns), it would imply that the DNA sample is heterozygous for the SNP of interest. In other words, both target allele HFE-wt and HFE-SNP are present in the sample, and the individual is a carrier, as discussed above. If the rate of reaction in the wild-type primer 422 wells is significantly higher than in the SNP wells (indicated in Table 1 as + in the wild-type primer column and − in the SNP primer column), the sample is homozygous for the wild-type allele, and thus the individual is free of hemochromatosis associated with this particular locus. If the rate of reaction in the SNP primer wells is higher than in the wild-type wells (indicated in Table 1 as − in the wild-type primer column and + in the SNP primer column), then it implies that the sample is homozygous for the mutant (SNP) allele, and thus the disease state likely exists in the individual. In the case of hemochromatosis, an iron-transport deficiency in humans, a particular SNP is present on both gene copies in 90% of cases. If only one gene carries that SNP, then that individual does not exhibit symptoms of the disease but is instead a carrier.

Figure 6:
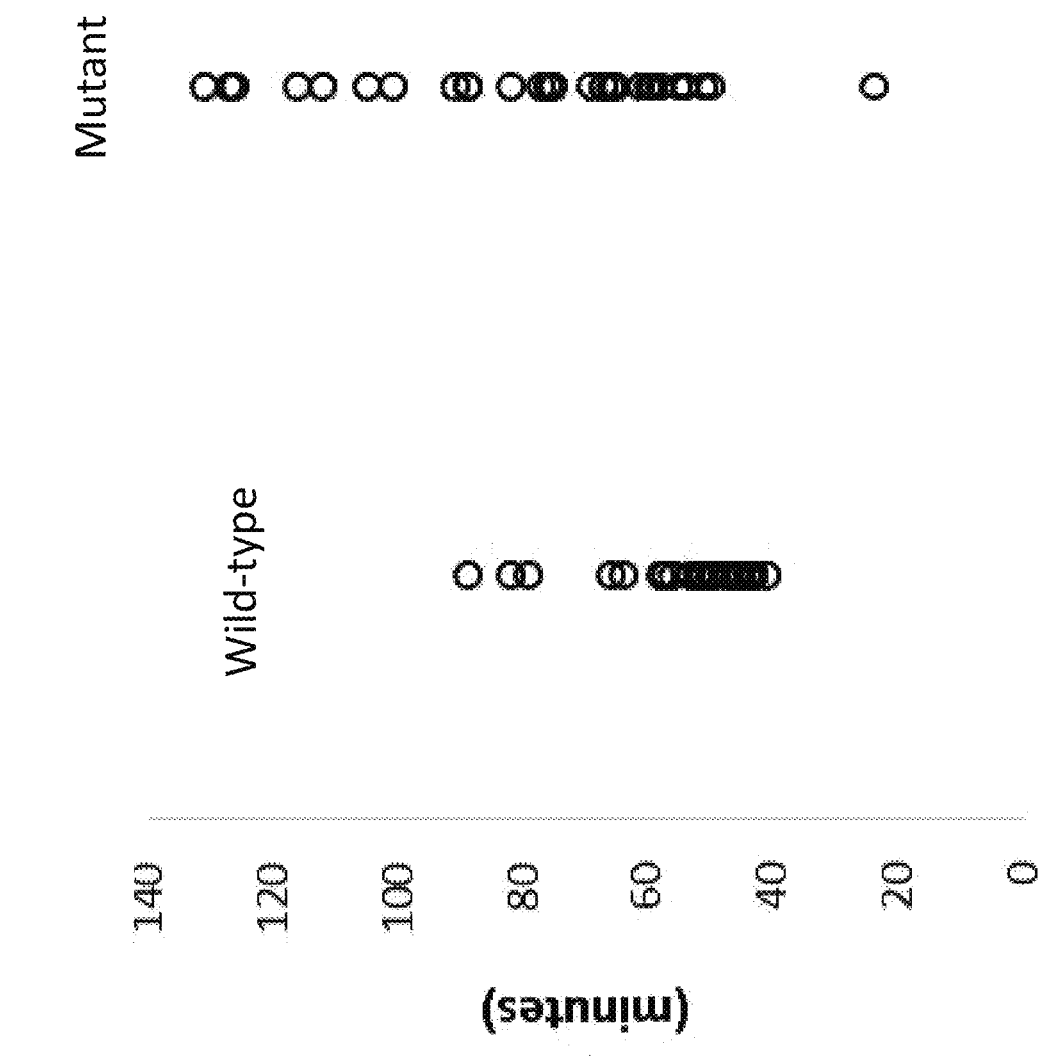
FIG. 6 is a graph of the result of an exemplary experiment.

A sample test is presented in FIG. 6, where a single base difference at the 5' end of the FIP primers results in differential response in a simulated homozygous, healthy sample containing only the wild-type allele on a recombinant plasmid. As the graph indicates, the wild-type primers' reactions are faster than those of mutant (SNP) primers. The number of wells preferred for a given assay may depend upon the differential capacity of a given SNP/wild-type primer set pair.

A preferred approach to reading the response of the multi-well reaction is to use a hand-held device, preferably one with a camera (such as a cell phone) with integrated software (such as a cell phone app) to both acquire images of the data and to conduct statistical analyses. The response characteristic for each primer set may be normalized to a reference LAMP reaction targeting a conserved region in the genome (reference reaction, as describe above). In accordance with a preferred embodiment, the response characteristic is either a 'yes/no' on the reaction status. Alternatively, the response characteristic may be the time it takes until a certain optical characteristic has been achieved, for example, the time of crossing of a threshold, similar to the cycle threshold value of PCR.

SNP Primer Competition Assays

An SNP test similar to that presented above may be conducted by creating a competition between SNP primers and wild-type primer, which are both present in a common well. The idea is to establish the proportion of wild-type vs. SNP primers that initiate a reaction. If the sample in a well reacts predominantly due to wild-type primers, then it may be inferred that the sample is homozygous for the wild-type allele. If the sample in a well reacts predominantly due to SNP primers, then it may be inferred that the sample is homozygous for the mutant allele. A mixed or ambiguous rate of reaction in a well may be associated with a heterozygous sample.

Figure 7:
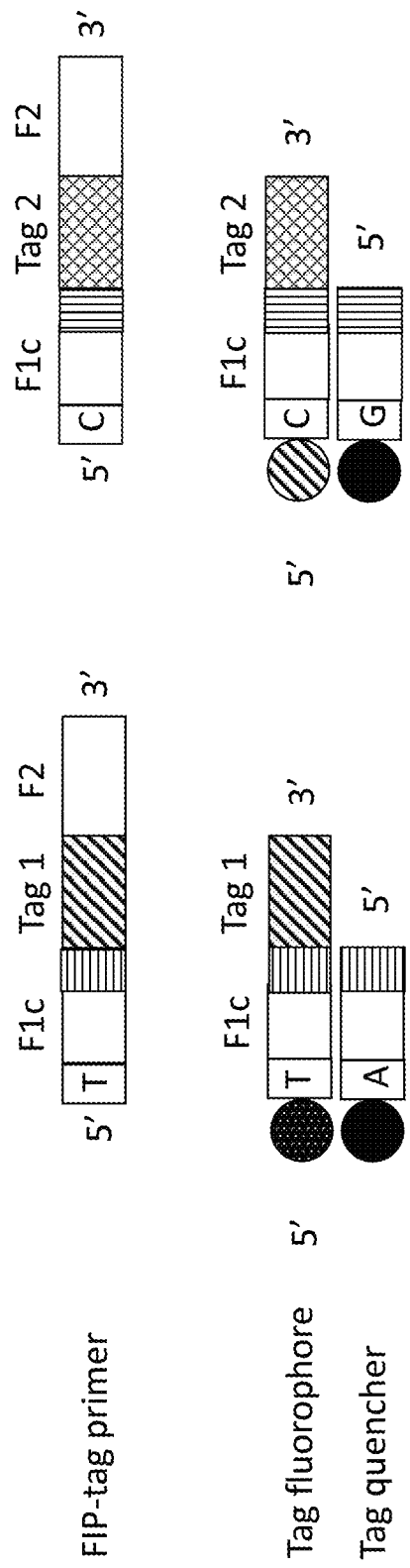
FIG. 7 is an illustration of a wild-type FIP-tag primer, SNP FIP-tag primer, and their corresponding tag fluorophore primers and tag quenchers in accordance with an embodiment of the invention.

The primers responsible for the LAMP reactions may be identified by incorporating a tag into each wild-type and/or mutant primer. Preferably, a tag fluorophore primer set is added which continues the LAMP reaction by recognizing the tag sequence, more preferably with an associated tag quencher. These primers are illustrated in FIG. 7. In accordance with an embodiment of the invention, these tagged primers are added to conventional LAMP primer mixtures, and the untagged FIP primers are removed. Whereas the spacer region between the tag and F1c of each primer may be different or the same for both the wild-type primer and the SNP primer, preferably, the spacer region is different as illustrated in FIG. 7. Providing a different spacer region for the wild-type primer from the SNP primer preferably increases the probability that the proper quencher and fluorophore sequences stay matched.

Figure 8:
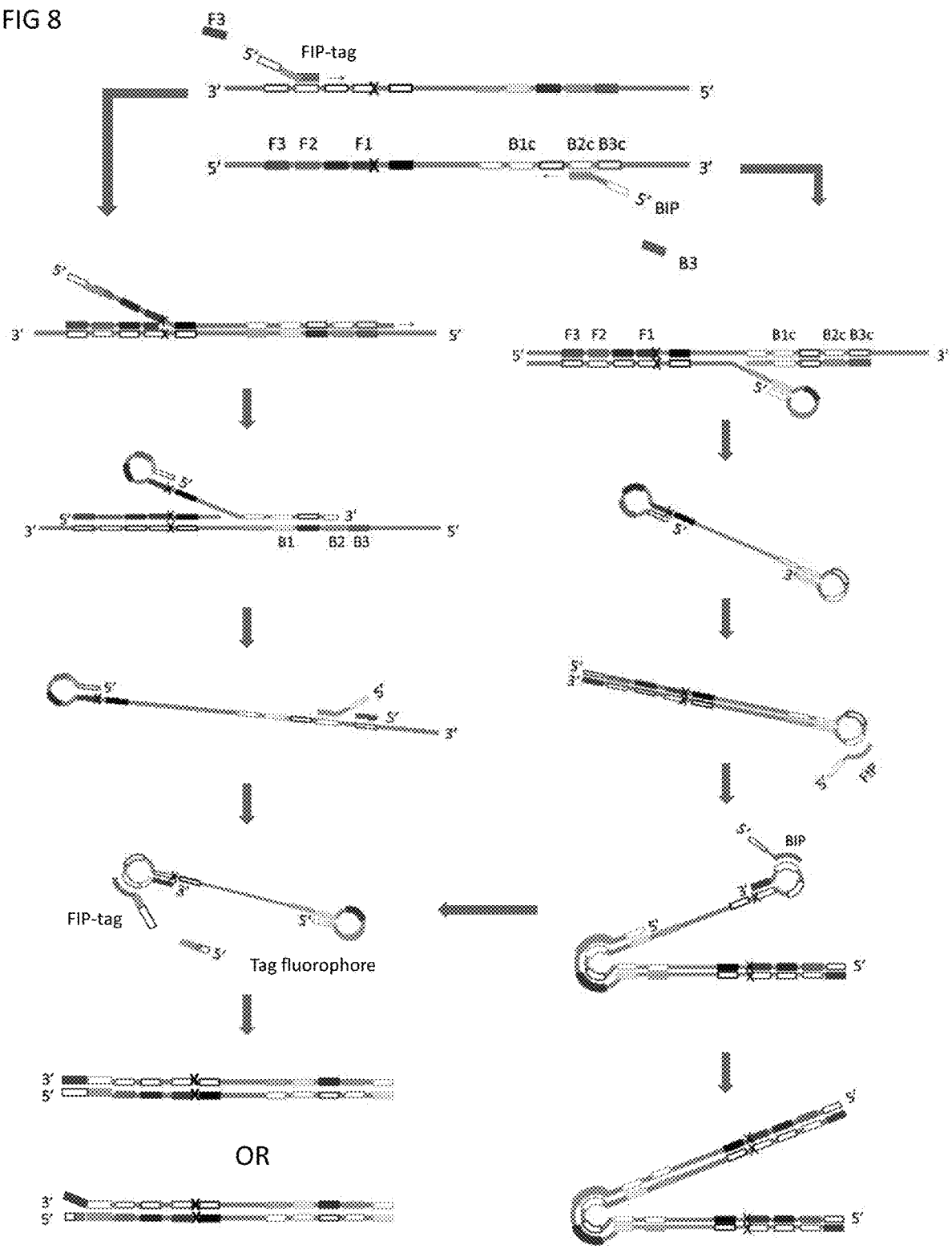
FIG. 8 is an illustration of a series of reactions in accordance with an embodiment of the invention.

An example of an SNP assay comprises two FIP-tag primers, one BIP primer, two tag fluorophores with two tag quenchers, and F3/B3 primers. Other primer sets known in the art may optionally be added. Preferably, these other primers include Loop (LF/LB) and Swarm (F1S/B1S). The reactions of wild-type FIP-tag primers preferably proceed according to the embodiment illustrated in FIG. 8. FIG. 8 shows the incorporation of a wild-type FIP-tag primer sequence into a growing amplicon, and the stifling of the reaction when the wild-type FIP primers are mismatched at the SNP (indicated as "X" in FIG. 8). Reactions may proceed according to conventional schemes when the primers do match the allele, with subsequent amplicon cycles initiated by either FIP-tag primers or Tag-fluorophore primers, which compete for the same spot on the allele. A reaction may comprise both wild-type FIP-tag primers and SNP FIP-tag primers, with their associated and distinct tags, and their tag-fluorophore/quencher pairs.

More specifically, a new reaction scheme that extends conventional LAMP reactions is introduced which establishes a two-part reaction. A first set of tagged FIP primers (one with a sequence to exactly match expected SNP sequences, one with a sequence to perfectly match wild-type) are introduced into a reaction. These primers, by creating novel recognition sequences in growing amplicons, enable subsequent reactions which produce tag-specific fluorescence markers.

Figure 9:
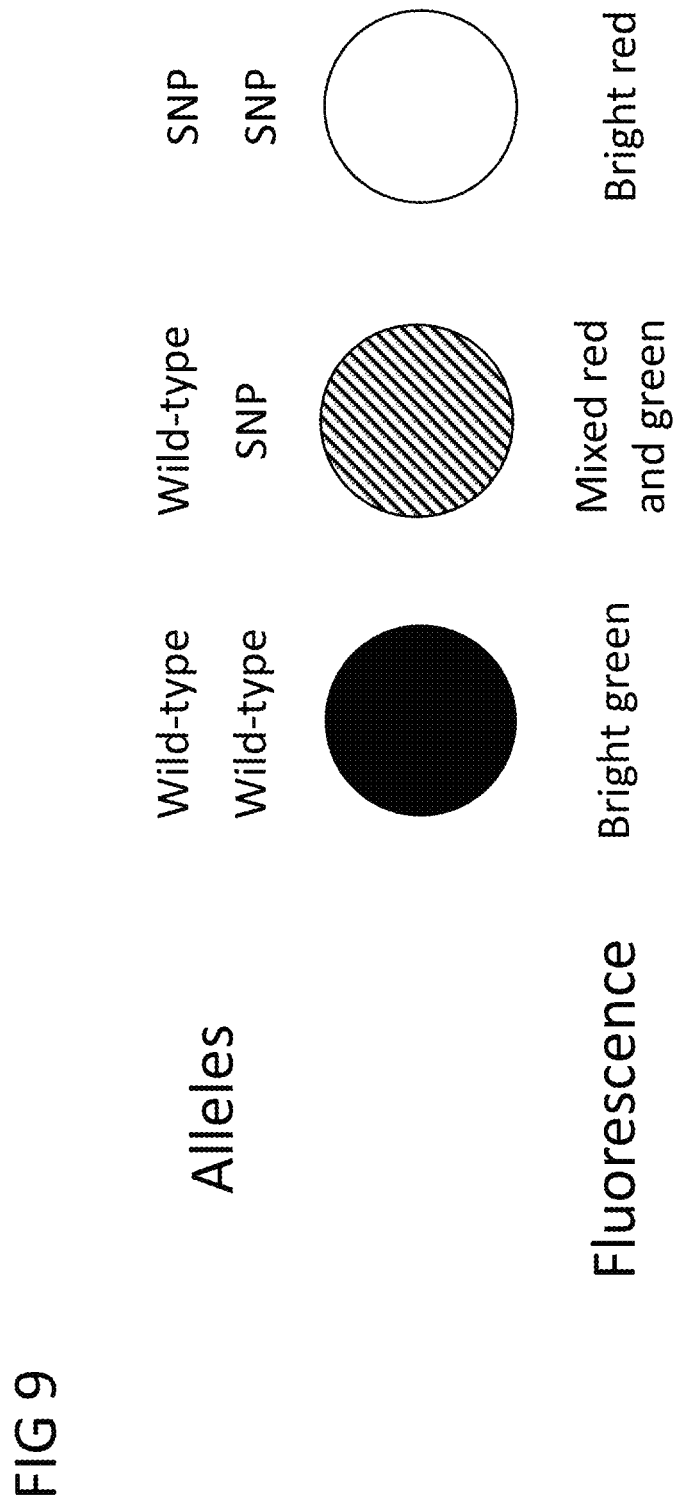
FIG. 9 is an illustration of the fluorescence results in accordance with an embodiment of the invention.

In general, the wild-type FIP-tag primers and SNP FIP-tag primers compete for template recognition sites on the alleles. A greater proportion of exactly matched primers will generally initiate the reaction and dominate. With each incorporation of the respective FIP-tag primer, there is a tag sequence in the single-stranded loop regions of growing amplicons which enable tag fluorophores to specifically bind as the reaction continues. Each specific tag fluorophore preferably has a distinct fluorophore attached at the 5' end as illustrated in FIG. 7. Preferably, tag fluorophores are supplied to the reaction with tag quenchers bound to each tag fluorophore. These primers generally operate in a manner similar to what is known as DARQ (detection of amplification by release of quenching) LAMP. When a particular tag fluorophore binds to a growing amplicon, subsequent reactions displace the associated quencher strand, producing bright fluorescence, as illustrated in FIG. 8. Thus, for example, wild-type primer reactions may be associated with green fluorescence, and mutant primer reactions can be associated with red fluorescence. In the embodiment illustrated in FIG. 9, the ratio of the two fluorescence signals at the end of a reaction indicates the proportion of wild-type alleles vs. SNP mutant alleles in the sample. Replication is recommended due to the frequency of non-specific reactions observed for LAMP reactions.

Other competitive approaches for highly specific/SNP detection are known in the art but differ from this invention at least in that the two primer sets used in the embodiments of the invention described herein tag growing amplicons and then measure the tags with a secondary reaction. No existing method takes this approach. Depending on the primer set and conditions of the reaction, an approach in accordance with an embodiment of the invention may be implemented in single wells or in arrays, as desired, to establish sufficient assay sensitivity and selectivity. This approach may be used as described using individual reaction wells or groups of wells, or in a modified fashion to establish the proportion of somatic (non germ-line) mutations in a population of cells, for example SNPs accumulating during cancer progression.

For example, in order to establish proportions of SNPs in a sample tumor tissue, droplet fluidics techniques may be incorporated as well. Dilution-to-extinction preferably enables reactions targeting a single template. In accordance with an exemplary embodiment, the reaction is primed with both sets of primers, the wild-type primer and SNP primer, and thus the SNP content of a sample may be established proportionally and/or absolutely with high precision and accuracy by counting the red and green droplets produced by analyzing a bulk sample. It may be more difficult to count droplets in bulk methods.

Furthermore, a pair of DARQ primers may be introduced into the reaction, with separate fluorophores to tag the sequences directly. Their competition, especially in multi-well format as presented here, may be used to type a DNA sample. DARQ primers, with attached quenchers/fluorophores, are known to inhibit LAMP reactions and to produce relatively high rates of false positives, thus requiring longer operation times and greater numbers of wells per SNP typing device. However, DARQ primers may be used in SNP discrimination as described herein.

By providing two primer sets whose reaction rates are discernibly different from each other, neither primer set needs to be perfect in its response. That is, the primer set that targets the wild-type need not react with 100% accuracy, and the primer set targeting the SNP need not react with 100% accuracy. Rather, the reaction rates of the two sets of primers are compared for relative performance and distinguished. If pairs of primer sets can react differentially, then it is possible to determine if there are one or two SNPs in a person's DNA, as indicated by Table 1. This preferably works for any SNP assessment in an organism that contains two copies of a gene of interest.

Compared to SNP literature which is generally directed to primers and methods which establish 100% rejection of incorrect single base mismatches or 100% acceptance of exactly matched primers, reagents that perform that perfectly are not needed to realize inexpensive and accurate SNP diagnostic devices according to the methods of this invention. Microfluidic partitioning of a sample into numerous wells, combined with statistical assessment of the relative speed or non-zero number of reactions is not taught in the art.

These embodiments of the invention preferably enable low-cost, automatable detection platforms with accuracy. The approaches and devices described preferably will enable untrained individuals with commonly available (household) items to be able to conduct highly accurate genotyping assays.

Whereas the embodiments discussed herein are directed to disease-screening based on a single SNP, other embodiments may be directed to numerous SNPs. For example, devices may be constructed which incorporate numerous SNP typing assays into a single chip, which may be analyzed in connection with each other (such as screening for each in a set of all SNPs known to cause hemochromatosis), or as independent assays for screening for multiple disease states (for example, hemochromatosis and rheumatoid arthritis). These methods may be extended by incorporating other LAMP reaction schemes known in the art, for example incorporation of double-mismatch primers discussed above.

Other alterations may be made without deviating from the scope of the invention. Accordingly, the system and method, the use, steps, order of steps, etc. may be varied as a matter of application specific design choice without deviating from the scope of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall there between.

We claim:

1. A method of detecting single nucleotide polymorphisms in nucleotide sequences by loop-mediated isothermal amplifications, said method comprising:
providing a plurality of wells comprising a first set of wells, a second set of wells, and a third set of wells;
providing a first target-specific primer in said first set of wells, wherein said first target-specific primer matches a wild-type allele at a first target;
providing a second target-specific primer in said second set of wells, said second target-specific primer having a 5' sequence different from said first target-specific primer, wherein said second target-specific primer matches a single nucleotide polymorphism allele at said first target;
providing a reference primer targeting a reference sequence in said third set of wells to target a conserved region in a targeted genome;
adding a sample nucleotide sequence into said first set of wells to start a first reaction between said first target-specific primer and said sample nucleotide sequence, wherein said first reaction produces a first color in the presence of said wild-type allele;
adding said sample nucleotide sequence into said second set of wells to start a second reaction between said second target-specific primer and said sample nucleotide sequence wherein said first reaction produces a second color different from said first color in the presence of said single nucleotide polymorphism allele; and
adding said sample nucleotide sequence into said third set of wells to start a reference reaction between said reference primer and said reference sequence, wherein said reference reaction produces a reference color different from said first color and said second color.

2. The method of claim 1, further comprising providing said first target-specific primer and a known concentration of a wild-type DNA having said wild-type allele into a fourth set of wells.

3. The method of claim 1, wherein said first target-specific primer and said second target-specific primer are forward inner primers.

4. The method of claim 1, wherein said first target-specific primer and said second target-specific primer are backward inner primers.

5. The method of claim 1, wherein said first target-specific primer has a first tag.

6. The method of claim 1, wherein said first target-specific primer has a first tag and said second target-specific primer has a second tag different from said first tag.

7. The method of claim 6, wherein said first target-specific primer has a first spacer region between said first tag and a first region, and said second target-specific primer has a second spacer region between said second tag and a second region, wherein said second spacer region is different from said first spacer region.

8. The method of claim 1, further comprising adding a tag fluorophore primer to said first set of wells and said second set of wells.

9. The method of claim 8, wherein said tag fluorophore primer is bound to a tag quencher.

10. The method of claim 9, further comprising adding each of a first tag fluorophore primer and a second tag fluorophore primer to each of said first set of wells and said second set of wells.

11. The method of claim 10, wherein the first tag fluorophore primer has a first fluorophore and the second tag fluorophore primer has a second fluorophore distinct from said first fluorophore.

12. The method of claim 8, wherein the tag fluorophore primer has a fluorophore attached at the 5' end.

* * * * *

SEQUENCE LISTING

<160> NUMBER OF SEQ ID NOS: 2

<210> SEQ ID NO 1
<211> LENGTH: 40
<212> TYPE: DNA
<213> ORGANISM: human

<400> SEQUENCE: 1
cacgtatatc tctgctcttg ggatgggacc taccagggct                          40

<210> SEQ ID NO 2
<211> LENGTH: 40
<212> TYPE: DNA
<213> ORGANISM: human

<400> SEQUENCE: 2
tacgtatatc tctgctcttg ggatgggacc taccagggct                          40